(12) United States Patent
Weissman et al.

(10) Patent No.: US 7,498,336 B2
(45) Date of Patent: Mar. 3, 2009

(54) DEAZAFLAVIN COMPOUNDS AND METHODS OF USE THEREOF

(75) Inventors: Allan M. Weissman, Bethesda, MD (US); Karen H. Vousden, Glasgow (GB); Jane P. Jensen, Potomac, MD (US); Yili Yang, Montgomery Village, MD (US); Shengyun Fang, Potomac, MD (US); Douglas Woods, Gaithersburg, MD (US); John H. Kenten, Boyds, MD (US); Ilia Davydov, North Potomac, MD (US); Yassamin J. Safiran, Potomac, MD (US); Pankaj Oberoi, Rockville, MD (US)

(73) Assignees: The United States of America as represented by the Secretary, Department of Health and Human Services, Washington, DC (US); BioVeris Corporation, Gaithersburg, MD (US)

( * ) Notice: Subject to any disclaimer, the term of this patent is extended or adjusted under 35 U.S.C. 154(b) by 0 days.

(21) Appl. No.: 10/545,547

(22) PCT Filed: Feb. 12, 2004

(86) PCT No.: PCT/US2004/004130

§ 371 (c)(1),
(2), (4) Date: Dec. 9, 2005

(87) PCT Pub. No.: WO2004/073615

PCT Pub. Date: Sep. 2, 2004

(65) Prior Publication Data

US 2006/0211718 A1  Sep. 21, 2006

Related U.S. Application Data

(60) Provisional application No. 60/447,610, filed on Feb. 13, 2003.

(51) Int. Cl.
*A01N 43/54* (2006.01)
*A61K 31/505* (2006.01)
*C07D 239/00* (2006.01)
*C07D 471/00* (2006.01)
*C07D 487/00* (2006.01)
*C07D 491/00* (2006.01)

(52) U.S. Cl. .................................. 514/267; 544/250
(58) Field of Classification Search ............... 544/250; 514/267
See application file for complete search history.

(56) References Cited

U.S. PATENT DOCUMENTS 5,858,976 A  1/1999 Burrell et al.

FOREIGN PATENT DOCUMENTS

| JP | 03-81276 | 5/1991 |
| JP | 2884170 | * 4/1999 |
| JP | 11-322746 | 11/1999 |
| JP | 2884170 | * 11/1999 |
| WO | WO-98/01467 | 1/1998 |
| WO | WO-98/15657 | 4/1998 |
| WO | WO-00/15657 | 3/2000 |

OTHER PUBLICATIONS

Freshney, Culture of Animal Cells, A Manual of Basic Technique, Alan R. Liss, Inc., 1983, New York, 4.*
Dermer, Another Anniversary for the War on Cancer, Bio/Technology, 1994, 12:320.*
Lubet, Ronald, et al., Use of p53 Transgenic Mice in the Development of Cancer Models for Multiple Purposes, Experimental Lung Research, 26,:581-593, 2000.*
Nagamatsu, T., et al., A New, General, and Convenient Synthesis of 5-Deazaflavins (5-Deazaisoalloxazines), J. Chem. Soc., Chem. Commun. (1982).*
Nagamatsu, et al., A New, General, and Convenient Synthesis of 5-Deazaflavins (5-Deazaisoalloxazines), J. Chem. Soc., Chem. Commun. (1982).*
Mikata et al., Bioorganic & Medicinal Chemistry Letters, 9:2141-2144 (1999).
T. Nagamatsu, et al., "Journ. of the Chem. Soc.", No. 18, pp. 1085-1086 (1982).
T. Nagamatsu et al., "Journ. of the Chem. Soc.", No. 3, pp. 561-565 (1984).

* cited by examiner

*Primary Examiner*—James O. Wilson
*Assistant Examiner*—Erich A Lesser
(74) *Attorney, Agent, or Firm*—Edwards Angell Palmer & Dodge LLP; Peter C. Corless; Nicholas J. DiCeglie, Jr.

(57) ABSTRACT

The present invention features 5-deazaflavin compounds, pharmaceutical compositions of 5-deazaflavin compounds and methods of treating a patient suffering from cancer, the method comprising administering to a patient one or more 5-deazaflavin compounds of the invention.

22 Claims, 6 Drawing Sheets

Inhibition of Mdm2 and Nedd4 auto-ubiquitination
Fig. 2A
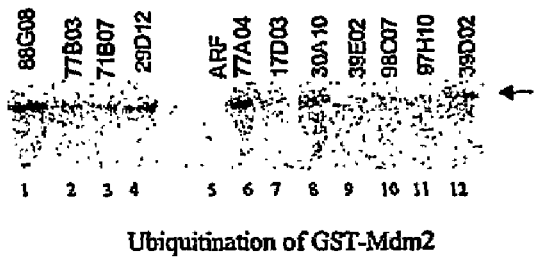
Ubiquitination of GST-Mdm2
Fig. 2B
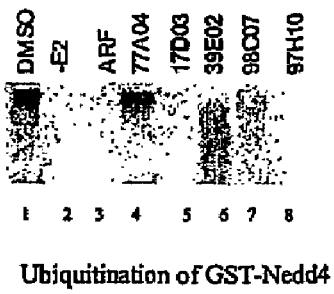
Ubiquitination of GST-Nedd4
Fig. 2C
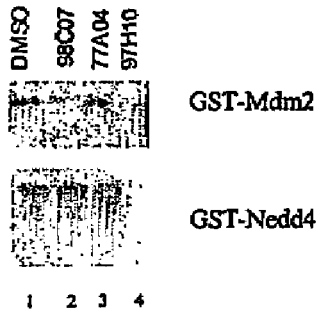
E1 and E2 Thiol-ester bond formation with Ubiquitin
Fig. 2D
Fig. 2E
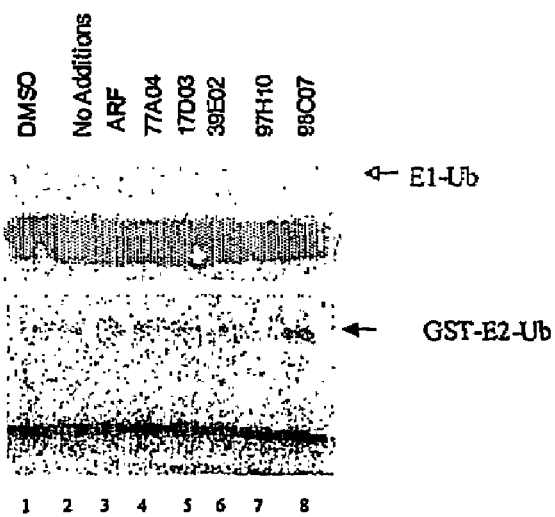

Ubiquitination of GST-Mdm2

98C07 and 98D07 inhibit p53 ubiquitylation by Mdm2

Screening hits from *in vitro* assay in cells
(MRC-5 1° human fibroblasts)

40 umolar 8 hr treatment

Specificity for Mdm2

The "98" compounds stabilize p53 and induce apoptosis in human RPE/E1A cells

A9: p53-/-
C8: p53+/+

A9: p53-/-
C8: p53+/+

DEAZAFLAVIN COMPOUNDS AND METHODS OF USE THEREOF

The present application claims the benefit of U.S. provisional application No. 60/447,610, filed Feb. 13, 2003, which is incorporated by reference herein in its entirety.

BACKGROUND OF THE INVENTION

1. Field of the Invention

The present invention involves 5-deazaflavin compounds and methods and pharmaceutical compositions that comprise such compounds. Compounds of the invention can be effective to regulate p53 and MDM2 stability and activity as well as to act as therapeutic agents in cancer.

2. Background

The development of cancer can depend on the accumulation of specific genetic alterations that allow aberrant cell proliferation, including growth of tumor cells. Protection from such aberrant growth is provided by several mechanisms that work by inducing apoptotic cell death in cells undergoing oncogenic changes. Therefore, for a tumor cell to survive, it must acquire genetic alterations that perturb the link between abnormal growth and cell death. The p53 tumor suppressor protein can induce apoptotic cell death and plays a pivotal role in tumor suppression. Wild type p53 functions as a transcriptional regulator to coordinately control multiple pathways in cell cycling, apoptosis, and angiogenesis.

Loss of the ability to induce p53 or other loss of p53 activity can lead to uncontrolled cell proliferation of the affected cells and tumor growth. In approximately 50% of human cancers, a wild type p53 gene is nevertheless retained. In such cancers, the defect that frequently occurs is a failure to stabilize and activate p53 to thereby prevent tumor development.

The MDM2 protein plays an important role in targeting the degradation of p53 in normal cells to allow normal growth and development. In particular, inhibition of MDM2 is required to allow activation of a p53 response. In tumors with wild type p53, defects can occur that lead to increased MDM2 activity, whereby p53 function cannot be induced.

Ubiquitin-mediated proteolysis is an important pathway of non-lysosomal protein degradation that controls the timed destruction of a number of cellular regulatory proteins including p53. See Pagano, 1997 FASEB J. 11:1067. Ubiquitin is an evolutionary highly conserved 76-amino acid polypeptide which is abundantly present in eukaryotic cells. The ubiquitin pathway leads to the covalent attachment of a poly-ubiquitin chain to target substrates which are then degraded by a multi-catalytic proteasome complex.

A number of the steps of regulating protein ubiquitination are known. In particular, initially the ubiquitin activating enzyme (E1) forms a high energy thioester linkage with ubiquitin. Ubiquitin is then transferred to a reactive cysteine residue of one of many ubiquitin conjugating enzymes known as Ubc or ubiquitin E2 enzymes. The final transfer of ubiquitin to a target protein involves one of many ubiquitin protein ligases (E3s). MDM2 is such a ubiquitin ligase that mediates the transfer of ubiquitin to p53.

It thus would be desirable to have new compounds that have use in treatment of undesired cell proliferation, including in treatment against cancer cells. It would be particularly desirable to have new compounds that could modulate or stabilize p53 activity by inhibiting MDM2-mediated ubiquitination.

SUMMARY OF THE INVENTION

The invention involves a family of 7-nitro-5-deazaflavin compounds. Compounds of the invention may be useful as anti-cancer agents. Indeed, we have found that 7-nitro-5-deazaflavin compounds can stabilize p53 in mammalian cells. Preferred 7-nitro-5-deazaflavin compounds additionally inhibit MDM2 activity. See for instance, the results set forth in the Examples, which follow.

More particularly, the invention provides compounds of the following Formula I:

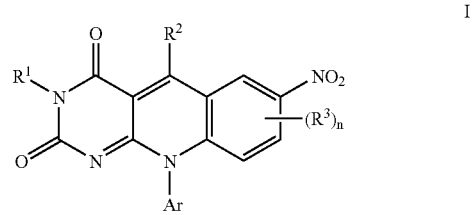

wherein:

Ar is a monosubstituted carbocyclic aryl group;

$R^1$ is selected from the group consisting of hydrogen, optionally substituted alkyl, optionally substituted alkenyl, optionally substituted alkynyl, optionally substituted carbocyclic aryl, optionally substituted heteroaryl, optionally substituted cycloalkyl, optionally substituted heteroalicyclic, or optionally substituted aminoalkyl;

$R^2$ and $R^3$ are independently selected from the group consisting of hydrogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mono- or di-alkyl amino, optionally substituted cycloalkyl, optionally substituted heteroalicyclic, or optionally substituted aminoalkyl; and n is an integer from 0 to 3; and pharmaceutically acceptable salts thereof.

These compounds exhibit detectable inhibition of MDM2 E3 ubiquitin ligase activity in an in vitro assay (defined herein as a "standard MDM2 activity in vitro assay"), particularly a detectable decrease in MDM2 ubiquitination as measured by a decrease in the addition of ubiquitin molecules to MDM2 as assessed using an SDS-PAGE gel based means of assessment. See the assay of Example 2, which follows. The protocol of that assay of Example 2 is defined herein to be a "standard MDM2 activity in vitro assay".

Particularly preferred compounds of the invention also may be selective for cancer cells relative to normal cells of a subject, i.e., such preferred compounds will exhibit reduced cell death in normal cells relative to targeted cancer cells. In particular, such preferred compounds can inhibit proliferation or induce apoptosis of targeted cancer cells, without exerting significant toxicity to normal (non-cancer) cells that may be contacted with the administered compound(s).

Compounds of the invention are useful for a number of therapeutic applications. In particular, the invention includes methods for treatment and prophylaxis of cancer, including cancers of the breast, lung, prostate, brain, liver, testes, skin, among others. Disseminated cancers (e.g., leukemias) as well as solid tumors may be treated by methods of the invention. Treatment methods of the invention may include administration of an effective amount of one or more compounds of the invention to cancer cells, such as those mentioned above. More particular methods include administering an effective amount of a compound of the invention to a subject such as a mammal, particularly a primate, e.g., a human that is suffering from or susceptible to (prophylactic treatment) abnormal cell proliferation, especially a cancer, such as a cancer mentioned above. Preferably, a subject is identified and selected that is susceptible or suffering undesired cell growth, especially cancer, such as a cancer mentioned above. An effective amount of one or more compounds of the invention suitably is an amount of one or more of the compounds of the invention sufficient to stabilize p53 in cells. The invention also includes use of one or more compounds disclosed herein, in combination or coordination with existing chemotherapies and/or radiotherapeutic protocols.

The invention also includes methods to stabilize p53 in cells, particularly mammalian cells, such as primate cells especially human cells.

Preferred methods of the invention are suitable for use in tumor growth regulation and comprise the administration of compounds of Formula I to targeted cells.

In a further aspect, the invention provides use of a compound of Formulae I, II, III and/or IV as defined herein, for the treatment or prevention (including prophylactic treatment) of a disease or condition as disclosed herein, including treatment or prevention of cancer or other undesired cell growth or proliferation.

In a yet further aspect, the invention provides use of a compound of Formulae I, II, III and/or IV as defined herein, for the preparation of a medicament for the treatment or prevention (including prophylactic treatment) of a disease or condition as disclosed herein, including treatment or prevention of cancer or other undesired cell growth or proliferation.

Pharmaceutical compositions also are provided which comprise a compound of Formulae I, II, III or IV as defined herein, optionally in combination with a pharmaceutically acceptable carrier. Preferably, such pharmaceutical compositions are packaged together with instructions (written) for use of the compounds for a therapeutic application, particularly to treat a subject for undesired cell growth, such as a cancer identified above.

The invention further provides methods for identifying (e.g., through screening) other compounds possessing activity as anti-cancer agents. The assays are preferably based on measurement of inhibition of MDM2 ubiquitin ligase activity, such as by standard MDM2 activity in vitro assay. Potential inhibitors of MDM2 would regulate the stability and function of p53 and MDM2. Preferably the assays measure the self-ubiquitylation of MDM2 in the presence of candidate compounds. An increased inhibition of the self-ubiquitylation of MDM2 in the presence of candidate compounds, as compared to control samples is indicative of a potential anti-tumor compound. Preferably, a candidate compounds inhibits self-ubiquitylation of MDM2 by at least 20% greater as compared to a control (no candidate compound administered) as measured in a standard MDM2 activity in vitro assay, more preferably a candidate compound inhibits self-ubiquitylation of MDM2 by at least about 30%, 40%, 50%, 60%, 70%, 80%, 90% or 100% as compared to a control system (no candidate compound administered) as measured in a standard MDM2 activity in vitro assay. Additional in vitro assays of use in identifying agents include inhibition of p53 ubiquitination by MDM2 (described infra). In such an assay, p53 produced in human or mouse cells or translated in a cell free eukaryotic expression system is pre-bound to MDM2 and inhibition of p53 ubiquitination is assessed.

In another preferred embodiment, potential inhibitors of MDM2 that regulate the stability and function of p53, can be determined in a cell based assay. Potential inhibitors of MDM2 would regulate the stability and function of p53 and MDM2. Preferably, the assays measure number of cells undergoing apoptosis due to the inhibition of MDM2 induced p53 degradation in tumor cells in the presence and/or absence of candidate compounds as compared to normal cells in the presence and/or absence of candidate compounds. The assay can also measure stabilization of p53 and MDM2 in cells following treatment with one or more candidate compounds.

In such assays of the invention, an increase in the number of cells undergoing apoptosis in the presence of candidate compounds in tumor cells, as compared to normal untreated cells is indicative of a potential anti-tumor compound. Preferably a candidate compound increases apoptosis of tumor cells by at least 20% as compared to a control system (no candidate compound administered), more preferably a candidate compound increases apoptosis of a tumor cell by at least about 30%, 40%, 50%, 60%, 70%, 80%, 90% or 100% as compared to a control system (no candidate compound administered). That is, for example, 80% increase of apoptosis refers to number of cells still surviving as compared to the controls. Apoptosis is preferably measured by visual observation (e.g., blebbing or trypan blue retention). Nucleic acids from cells having undergone apoptosis can be run on gels showing the characteristic 200 bp nucleic acid ladder that is indicative of cells having undergone apoptosis, or cells with less than a G1 DNA content can be identified by fluorescence activated cell sorting. Other assays for apoptosis include TUNEL assays or detection of caspase activation.

Assays of the invention also are useful for assessing MDM2 inhibition is in in vitro and in vivo systems.

In another aspect, the invention includes compounds that can interact with E1 and/or E2 enzymes. Compounds that inhibit at E1 and/or E2 levels would be useful drug candidates that could indirectly interfere with the activity of ubiquitin ligases, particularly MDM2. Since interactions between E1 and E2 share similarities to those between E2 and E3, compounds of the invention may also inhibit loading of E2 by E1, and thereby, inhibit the activity of ubiquitin ligases such as MDM2.

Other aspects of the invention are described infra.

BRIEF DESCRIPTION OF DRAWINGS

FIGS. 2A-2G are gels showing the results obtained using in vitro gel assays. FIGS. 2A-2C shows the ubiquitination of MDM2 and Nedd4 in the presence or absence of candidate compounds.

FIG. 2A is a gel showing the inhibition of MDM2 ubiquitination in the presence or absence of candidate compounds. Using the ARF peptide as a positive control for inhibition of MDM2 ubiquitination, these assays identified four compounds that showed an ability to significantly inhibit MDM2 E3 ligase (FIG. 2A lanes 7, 9, 10, 11).

FIG. 2B is a gel showing typical results obtained in a screen to determine whether the compounds were selective in their ability to inhibit MDM2 as compared to their effect on the activity of another unrelated E3 ligase, Nedd4.

FIG. 2C is gel showing the results of an independent experiment further demonstrating the specificity of MDM2 by 98C07 (10-(-3-chloro-phenyl)-7-nitro-10H-pyrimido [4,5-b]quinoline-2,4-dione) (lane 2).

FIGS. 2D and 2E show the effect of compounds on the more proximal steps in the ubiquitination process, formation of thiol-ester linkages with E1 (FIG. 2D) and with E2 (FIG. 2E).

FIG. 2F shows inhibition of MDM2 auto-ubiquitination by two other close family members of 98C07.

FIG. 2G shows the results obtained from two compounds that inhibit p53 ubiquitination by MDM2. 98C07 and 98D07 (10-(-4-chloro-phenyl)-7-nitro-10H-pyrimido[4,5-b]quinoline-2,4-dione) both exhibit significant dose-dependent inhibition of p53 ubiquitination after cellular p53 is pre-bound to GST-MDM2.

As shown in FIG. 3B, they all increased MDM2 and p53 levels in MRC-5 cells. The specificity of the compounds was also revealed by examining whether they affect the levels of the HECT domain E3 Nedd4 and p27, which is ubiquitinated by a RING finger-dependent SCF E3. As shown in FIG. 3B, the amounts of both Nedd4 and p27 were not changed significantly by any of the 98 family compounds. Moreover, while adriamycin increased only p53 and proteosome inhibitor (LLNL) accumulated MDM2, p53, and p21, these compounds only increased the amount of MDM2 and p53, but not p21, indicating they are specific for the E3 activity of MDM2 (FIG. 3C).

DETAILED DESCRIPTION OF THE INVENTION

Figure 1:
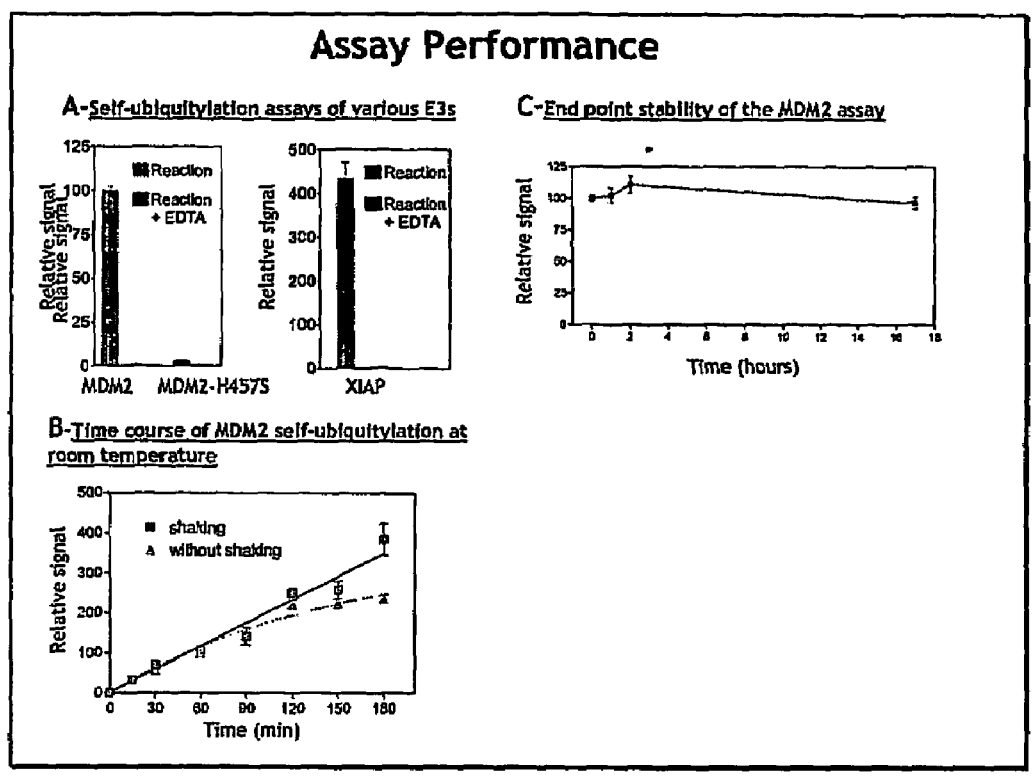
FIG. 1A is a graph showing that MDM2 exhibited a signal to background ratio of ~100 in self-ubiquitylation assay. Time course of MDM2 self-ubiquitylation revealed linear reaction kinetics and no benefit of shaking within the first 60 min. Samples were incubated at room temperature and not shaken for ease of automation as shown in FIG. 1B.
FIG. 1C is a graph showing that the MDM2 assay signal is a function of time between addition of the antibody and measuring in an M8 analyzer.

As discussed above, we now provide new 7-nitro-5-deazaflavin compounds which can be useful in cancer therapies.

Preferred compounds of Formula I of the invention include those of the following Formula II:

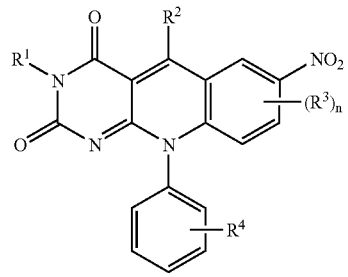

wherein:

$R^1$ is selected from the group consisting of hydrogen, optionally substituted alkyl, optionally substituted alkenyl, optionally substituted alkynyl, optionally substituted carbocyclic aryl, optionally substituted heteroaryl, optionally substituted cycloalkyl, optionally substituted heteroalicyclic, or optionally substituted aminoalkyl;

$R^2$ and $R^3$ are independently selected from the group consisting of hydrogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mono- or di-alkyl amino, optionally substituted cycloalkyl, optionally substituted heteroalicyclic, or optionally substituted aminoalkyl;

$R^4$ is selected from the group consisting of amino, halogen, hydroxy, cyano, nitro, carboxylate, carboxamide, optionally substituted alkyl, optionally substituted alkenyl, optionally substituted alkynyl, optionally substituted aryl, optionally substituted heteroaryl, optionally substituted alkoxy, optionally substituted mono- or di-alkyl amino, optionally substituted cycloalkyl, optionally substituted heteroalicyclic, or optionally substituted aminoalkyl; and n is an integer from 0 to 3; and pharmaceutically acceptable salts thereof.

Particularly preferred compounds of Formula II provided by the invention include those compounds in which $R^1$ is selected from the group consisting of hydrogen, $C_{1-6}$alkyl, $C_{2-6}$alkenyl, $C_{2-6}$alkynyl, $C_{1-6}$hydroxyalkyl, $C_{1-6}$aminoalkyl, $C_{6-12}$aryl, $C_{3-12}$heteroaryl having between 1 and 4 ring heteroatoms, $C_{7-12}$aralkyl, $C_{3-12}$cycloalkyl, and $C_{3-12}$cycloheteroalkyl;

$R^2$ and $R^3$ are independently selected from the group consisting of hydrogen, amino, hydroxy, cyano, nitro, $C_{1-6}$alkyl, $C_{2-6}$alkenyl, $C_{2-6}$alkynyl, $C_{1-6}$alkoxy, $C_{1-6}$hydroxyalkyl, $C_{1-6}$aminoalkyl, $C_{6-12}$aryl, $C_{3-12}$heteroaryl having between 1 and 4 ring heteroatoms, $C_{7-12}$aralkyl, $C_{3-12}$cycloalkyl, $C_{3-12}$cycloheteroalkyl, mono or di ($C_{1-6}$alkyl)amino, or carboxylate;

$R^4$ is selected from the group consisting of amino, halogen, hydroxy, $C_{1-6}$alkyl, $C_{2-6}$alkenyl, $C_{2-6}$alkynyl, $C_{1-6}$alkoxy, or mono or di ($C_{1-6}$alkyl)amino; and n is an integer from 0 to 3; and pharmaceutically acceptable salts thereof.

Other preferred compounds according to Formula I or Formula II include those represented by the following Formula III:

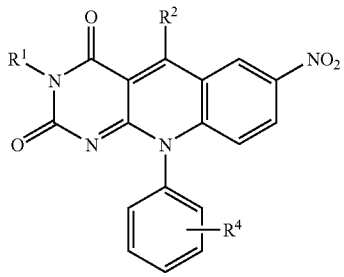

R[1] is selected from the group consisting of hydrogen, $C_{1-6}$alkyl, $C_{2-6}$alkenyl, $C_{2-6}$alkynyl, $C_{1-6}$hydroxyalkyl, $C_{1-6}$aminoalkyl, $C_{6-12}$aryl, $C_{3-12}$heteroaryl having between 1 and 4 ring heteroatoms, $C_{7-12}$aralkyl, $C_{3-12}$cycloalkyl, and $C_{3-12}$cycloheteroalkyl;

R[2] is selected from the group consisting of hydrogen, amino, hydroxy, cyano, nitro, $C_{1-6}$alkyl, $C_{2-6}$alkenyl, $C_{2-6}$alkynyl, $C_{1-6}$alkoxy, $C_{1-6}$hydroxyalkyl, $C_{1-6}$aminoalkyl, $C_{6-12}$aryl, $C_{3-12}$heteroaryl having between 1 and 4 ring heteroatoms, $C_{7-12}$aralkyl, $C_{3-12}$cycloalkyl, $C_{3-12}$cycloheteroalkyl, mono or di ($C_{1-6}$alkyl)amino, or carboxylate;

R[4] is selected from the group consisting of amino, halogen, hydroxy, $C_{1-6}$alkyl, $C_{2-6}$alkenyl, $C_{2-6}$alkynyl, $C_{1-6}$alkoxy, or mono or di ($C_{1-6}$alkyl)amino; and n is an integer from 0 to 3; and pharmaceutically acceptable salts thereof.

Particularly preferred compounds of any one of Formula I, II, or III provided by the invention include those compounds wherein R[1], R[2], and each occurrence of R[3] are selected from the group consisting of hydrogen and $C_{1-6}$alkyl; and R[4] is selected from the group consisting of chloro, fluoro, bromo, methyl, ethyl, hydroxy, and methoxy.

Additionally preferred compounds of the present invention include those compounds of the following Formula IV:

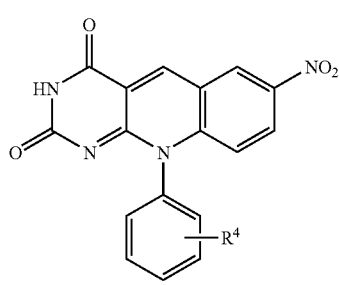

wherein R[4] is selected from the group consisting of amino, halogen, hydroxy, $C_{1-6}$alkyl, $C_{2-6}$alkenyl, $C_{2-6}$alkynyl, $C_{1-6}$alkoxy, or mono or di ($C_{1-6}$alkyl)amino; and pharmaceutically acceptable salts thereof.

Particularly preferred compounds according to Formula IV include those wherein R[4] is selected from the group consisting of a chloro, fluoro, or methyl group, and R[4] is attached to the 3 or 4 position of the phenyl ring.

Other particularly preferred compounds provided by the invention include the following, where the compound structure is depicted directly above the compound name.

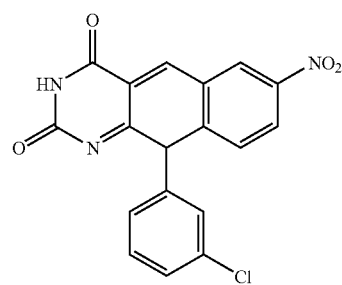

10-(3-chloro-phenyl)-7-nitro-10H-pyrimido[4,5-b]quinoline-2,4-dione,

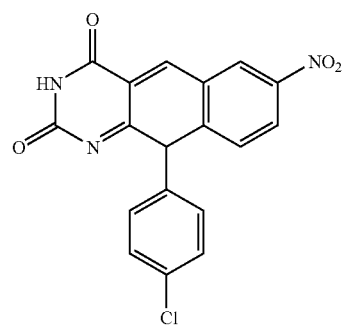

10-(4-chloro-phenyl)-7-nitro-10H-pyrimido[4,5-b]quinoline-2,4-dione, and

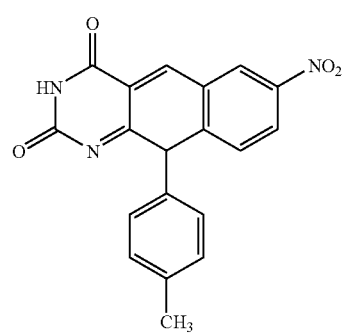

10-(4-methyl-phenyl)-7-nitro-10H-pyrimido[4,5-b]quinoline-2,4-dione.

Suitable alkyl substituent groups of compounds of the invention (which includes compounds of Formulae I, II, III and IV as defined above) typically have from 1 to about 12 carbon atoms, more preferably 1 to about 8 carbon atoms, still more preferably 1, 2, 3, 4, 5, or 6 carbon atoms. As used herein, the term alkyl unless otherwise modified refers to both cyclic and noncyclic groups, although of course cyclic groups will comprise at least three carbon ring members. Preferred alkenyl and alkynyl groups of compounds of the invention have one or more unsaturated linkages and typically from 2 to about 12 carbon atoms, more preferably 2 to about 8 carbon atoms, still more preferably 2, 3, 4, 5, or 6 carbon atoms. The terms alkenyl and alkynyl as used herein refer to both cyclic and noncyclic groups, although straight or branched noncyclic groups are generally more preferred. Preferred alkoxy groups of compounds of the invention include groups having one or more oxygen linkages and from 1 to about 12 carbon atoms, more preferably from 1 to about 8 carbon atoms, and still more preferably 1, 2, 3, 4, 5 or 6 carbon atoms. Preferred alkylthio groups of compounds of the invention include those groups having one or more thioether linkages and from 1 to about 12 carbon atoms, more preferably from 1 to about 8 carbon atoms, and still more preferably 1, 2, 3, 4, 5, or 6 carbon atoms. Preferred alkylsulfinyl groups of compounds of the invention include those groups having one or more sulfoxide (SO) groups and from 1 to about 12 carbon atoms, more preferably from 1 to about 8 carbon atoms, and still more preferably 1, 2, 3, 4, 5, or 6 carbon atoms. Preferred alkylsulfonyl groups of compounds of the invention include those groups having one or more sulfonyl ($SO_2$) groups and from 1 to about 12 carbon atoms, more preferably from 1 to about 8 carbon atoms, and still more preferably 1, 2, 3, 4, 5 or 6 carbon atoms. Preferred aminoalkyl groups include those groups having one or more primary, secondary and/or tertiary amine groups, and from 1 to about 12 carbon atoms, more preferably 1 to about 8 carbon atoms, still more preferably 1, 2, 3, 4, 5, or 6 carbon atoms. Secondary and tertiary amine groups are generally more preferred than primary amine moieties. Suitable heteroaromatic groups of compounds of the invention contain one or more N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazole. Suitable heteroalicyclic groups of compounds of the invention contain one or more N, O or S atoms and include, e.g., tetrahydrofuranyl, thienyl, tetrahydropyranyl, piperidinyl, morpholino and pyrrolidinyl groups. Suitable carbocyclic aryl groups of compounds of the invention include single and multiple ring compounds, including multiple ring compounds that contain separate and/or fused aryl groups. Typical carbocyclic aryl groups of compounds of the invention contain 1 to 3 separate or fused rings and from 6 to about 18 carbon ring atoms. Specifically preferred carbocyclic aryl groups include phenyl; naphthyl including 1-naphthyl and 2-naphthyl; biphenyl; phenanthryl; anthracyl; and acenaphthyl. Substituted carbocyclic groups are particularly suitable including substituted phenyl, such as 2-substituted phenyl, 3-substituted phenyl, 4-substituted phenyl, 2,3-substituted phenyl, 2,4-substituted phenyl, and 2,4-substituted phenyl; and substituted naphthyl, including naphthyl substituted at the 5, 6 and/or 7 positions.

Suitable aralkyl groups of compounds of the invention include single and multiple ring compounds, including multiple ring compounds that contain separate and/or fused aryl groups. Typical aralkyl groups contain 1 to 3 separate or fused rings and from 6 to about 18 carbon ring atoms. Preferred aralkyl groups include benzyl and methylenenaphthyl (—$CH_2$-naphthyl), and other carbocyclic aralkyl groups, as discussed above.

Suitable heteroaralkyl groups of compounds of the invention include single and multiple ring compounds, including multiple ring compounds that contain separate and/or fused heteroaromatic groups, where such groups are substituted onto an alkyl linkage. More preferably, a heteroaralkyl group contains a heteroaromatic group that has 1 to 3 rings, 3 to 8 ring members in each ring and from 1 to 3 hetero (N, O or S) atoms, substituted onto an alkyl linkage. Suitable heteroaromatic groups substituted onto an alkyl linkage include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazole.

Suitable heteroalicyclicalkyl groups of compounds of the invention include single and multiple ring compounds, where such groups are substituted onto an alkyl linkage. More preferably, a heteroalicylicalkyl group contains at least one ring that has 3 to 8 ring members from 1 to 3 hetero (N, O or S) atoms, substituted onto an alkyl linkage. Suitable heteroalicyclic groups substituted onto an alkyl linkage include, e.g. tetrahydrofuranyl, thienyl, tetrahydropyranyl, piperidinyl, morpholino and pyrrolidinyl groups.

As discussed above, various substituent groups ($R^2$, $R^3$, and $R^4$) of Formulae I through IV may be optionally substituted. A "substituted" $R^1$, $R^2$, $R^3$, and $R^4$ group or other substituent may be substituted by other than hydrogen at one or more available positions, typically 1 to 3 or 4 positions, by one or more suitable groups such as those disclosed herein. Suitable groups that may be present on a "substituted" $R^1$, $R^2$, $R^3$, and $R^4$ group or other substituent include e.g. halogen such as fluoro, chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms, or 1, 2, 3, 4, 5, or 6 carbon atoms; alkenyl and alkynyl groups including groups having one or more unsaturated linkages and from 2 to about 12 carbon, or 2, 3, 4, 5 or 6 carbon atoms; alkoxy groups having those having one or more oxygen linkages and from 1 to about 12 carbon atoms, or 1, 2, 3, 4, 5 or 6 carbon atoms; aryloxy such as phenoxy; alkylthio groups including those moieties having one or more thioether linkages and from 1 to about 12 carbon atoms, or 1, 2, 3, 4, 5 or 6 carbon atoms; alkylsulfinyl groups including those moieties having one or more sulfinyl linkages and from 1 to about 12 carbon atoms, or 1, 2, 3, 4, 5, or 6 carbon atoms; alkylsulfonyl groups including those moieties having one or more sulfonyl linkages and from 1 to about 12 carbon atoms, or 1, 2, 3, 4, 5, or 6 carbon atoms; aminoalkyl groups such as groups having one or more N atoms and from 1 to about 12 carbon atoms, or 1, 2, 3, 4, 5 or 6 carbon atoms; carbocyclic aryl having 6 or more carbons, particularly phenyl (e.g. an R group being a substituted or unsubstituted biphenyl moiety); aralkyl having 1 to 3 separate or fused rings and from 6 to about 18 carbon ring atoms, with benzyl being a preferred group; aralkoxy having 1 to 3 separate or fused rings and from 6 to about 18 carbon ring atoms, with O-benzyl being a preferred group; or a heteroaromatic or heteroalicyclic group having 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofaranyl, tetrahydropyranyl, piperidinyl, morpholino and pyrrolidinyl.

Compounds of the invention may exist in differing isomeric forms, including as differing stereoisomers, geometric isomers and the like. Compounds suitable for use in the methods of the present invention include any and all different single pure isomers and mixtures of two or more isomers. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with a enantiomerically enriched compound, a racemate, or a mixture of diastereomers. Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral 7-nitro-5-deazaflavin compound is administered to cells or a subject.

Compounds of the invention can be readily prepared by known synthetic methods. For example, a compound of Formula I may be prepared by cyclocondensation of a 6-(N-arylamino)uracil and a 2-halo-5-nitro-benzaldehyde to form 10-aryl-7-nitro-5-deazaflavin compounds. In other embodiments, various compounds of the invention can be readily prepared having a variety of functionalized aryl groups by synthesizing 7-nitro-5-deazaflavin compounds which are unsubstituted at the 10 position from 6-aminouracil and a 2-halo-5-nitro-benzaldehyde compound. Subsequent arylation at the 10 position may be carried out in any convenient manner such as palladium/phosphine catalyzed arylation of the 7-nitro-5-deazaflavin compound with an activated aryl reagent such as an aryl bromide, aryl iodide, aryl boronic acid, aryl tin reagent, aryl silane, or the like.

As discussed above, it has been found that 7-nitro-5-deazaflavin compounds of the present invention including those compounds represented by any one of Formula I-IV are capable of stabilizing p53. Although not being bound by any theory, it is believed that preferred compounds of the invention can stabilize p53 activity in transformed cells by inhibition of MDM2 ubiquitin ligase activity. More particularly, it is believed compounds of the invention, including those compounds of Formula I-IV, are capable of inhibiting the ubiquitin ligase (E3) activity of MDM2.

As discussed above, the invention includes methods for treating or preventing (prophylactic treatment) against undesired cell growth or proliferation.

Preferred therapeutic methods of the invention include treating malignancies, including solid tumors and disseminated cancers. Exemplary tumors that may be treated in accordance with the invention include e.g. cancers of the lung, prostate, breast, liver, colon, breast, kidney, pancreas, brain, skin including malignant melanoma and Kaposi's sarcoma, testes or ovaries, or leukemias or lymphomia including Hodgkin's disease.

The therapeutic methods of the invention generally comprise administration of an effective amount of one or more compounds of the invention to a subject including a mammal, such as a primate, especially a human, in need of such treatment.

The treatment methods of the invention also will be useful for treatment of mammals other than humans, including for veterinary applications such as to treat horses and livestock e.g. cattle, sheep, cows, goats, swine and the like, and pets (companion animals) such as dogs and cats.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum, cellular interstitial fluid, saliva, feces and urine) and cell and tissue samples of the above subjects will be suitable for use.

Compounds of the invention may be administered singularly (i.e., sole therapeutic agent of a regime) to treat or prevent diseases and conditions such as undesired cell proliferation as disclosed herein.

Compounds of the invention also may be administered as a "cocktail" formulation, i.e., coordinated administration of one or more compounds of the invention together with one or more other active therapeutics. For instance, one or more compounds of the invention may be administered in coordination with a regime of one or more other chemotherapeutic agents, particularly a compound that functions against cancer cells other than by p53 stabilization such as an antineoplastic drug, e.g., an alkylating agent (e.g., mechloroethamine, chlorambucil, cyclophosamide, melphalan, or ifosfamide), an antimetabolite such as a folate antagonist (e.g., methotrexate), a purine antagonist (e.g. 6-mercaptopurine) or a pyrimidine antagonist (e.g., 5-fluorouracil). Other, non-limiting examples of chemotherapeutic agents that might be used in coordination with one or more compounds of the invention include taxanes and topoisomerase inhibitors. In addition, other non-limiting examples of active therapeutics include biological agents, such as monoclonal antibodies or IgG chimeric molecules, that achieve their therapeutic effect by specifically binding to a receptor or ligand in a signal transduction pathway associated with cancer.

A particularly suitable combination protocol may include coordinated administration of one or more compounds of the invention with a compound that can activate but not necessarily stabilize p53, e.g. a therapeutic agent that can enhance interaction of p53 with histone acetylases.

Compounds of the invention can be administered by a variety of routes, such as orally or by injection, e.g., intramuscular, intraperitoneal, subcutaneous or intravenous injection, or topically such as transdermally, vaginally and the like.

In a most preferred embodiment, the compounds of the invention are administered intravenously. Compounds of the invention may be suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc. If the compound has an acidic group, e.g. a carboxy group, base additional salts may be prepared. Lists of additional suitable salts may be found, e.g., in Remington's Pharmaceutical Sciences, $17^{th}$ ed., Mack Publishing Company, Easton, Pa.

Compounds of the invention can be employed, either alone or in combination with one or more other therapeutic agents as discussed above, as a pharmaceutical composition in mixture with conventional excipient, i.e., pharmaceutically acceptable organic or inorganic carrier substances suitable for oral, parenteral, enteral or topical application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Pharmaceutical compositions of the invention include a compound of the invention packaged together with instructions (written) for therapeutic use of the compound, particularly to treat a subject suffering from or susceptible to cancer. Most preferred method of treating the patient with the pharmaceutical compositions of the invention, is administration of the compositions intravenously. However, other routes of administration of the pharmaceutical compositions can be used.

For oral administration, pharmaceutical compositions containing one or more compounds of the invention may be formulated as e.g. tablets, troches, lozenges, aqueous or oily suspensions, dispersible powders or granules, emulsions, hard or soft capsules, syrups, elixers and the like. Typically suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

For parenteral application, e.g., sub-cutaneous, intraperitoneal or intramuscular, particularly suitable are solutions, preferably oily or aqueous solutions as well as suspensions, emulsions, or implants, including suppositories. Ampoules are convenient unit dosages.

The actual amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. See also Remington's Pharmaceutical Sciences, supra. In general, a suitable effective dose of one or more compounds of the invention, particularly when using the more potent compound(s) of the invention, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day. The desired dose is suitably administered once daily, or several sub-doses, e.g. 2 to 4 sub-doses, are administered at appropriate intervals through the day, or other appropriate schedule. Such sub-doses may be administered as unit dosage forms, e.g., containing from 0.05 to 10 milligrams of compound(s) of the invention, per unit dosage.

As discussed above, the invention also provides methods (also referred to herein as "screening assays") for identifying candidate compounds useful for treatment against cancer cells or other undesired cell proliferation. Screening assays can be adapted to a high throughput format to enable the rapid screening of a large number of compounds. Assays and screening methods can be used for identification of compounds possessing MDM2-specific and/or general inhibition of ubiquitin enzyme inhibitory activity. Thus, in accordance with the invention, methods are provided to screen candidate compounds which exhibit potential anti-cancer activity by measuring p53 stability in transformed cells and/or apoptosis and cell death.

MDM2 protein binds tumor suppressor p53 and targets it for ubiquitylation and proteosome-mediated degradation. MDM2 is a RING finger-containing E3 ubiquitin ligase for p53. MDM2 also catalyzes self-ubiquitylation, and thus regulates intracellular levels of both p53 and itself. Without wishing to be bound by theory, molecules which inhibit the binding of MDM2 to p53 could be important in identifying potential drug compounds that inhibit MDM2 ligase activity that affects p53 stability. Similarly, interference with the expression of MDM2 by a candidate drug compound can identify anti-tumor compounds that can be further analyzed using a high-throughput assay described below. As a theoretical illustrative example, expression may be down regulated by administering small molecules and peptides which specifically inhibit MDM2 expression can also be used.

In theory, such inhibitory molecules can be identified by screening for interference of the MDM2/p53 interaction where one of the binding partners is bound to a solid support and the other partner is labeled. Antibodies specific for epitopes on MDM2 or p53 which are involved in the binding interaction will interfere with such binding. Solid supports which may be used include any polymers which are known to bind proteins. The support may be in the form of a filter, column packing matrix or sephadex beads. Labeling of proteins can be accomplished according to many techniques. Radiolabels, enzymatic labels, and fluorescent labels can be used. Alternatively, both MDM2 and p53 may be in solution and bound molecules separated from unbound subsequently. Any separation technique may be employed, including immunoprecipitation or immunoaffinity separation with an antibody specific for the unlabeled binding partner.

For in vitro assays MDM2 can be expressed as a GST fusion. This allows for a high level of expression of protein that can be purified on glutathione Sepharose. Detection of ubiquitination of MDM2 can be accomplished, for example, using $^{32}$P-labeled ubiquitin, Western blotting with anti-ubiquitin, or by looking at a shift in the molecular weight of GST fusion by Western blotting with anti-GST. A variety of in vitro assays that measure levels of self-ubiquitylated MDM2 can be employed, such as for example, immunoprecipitation of ubiquitylated MDM2; gel assays wherein the amount of ubiquitylated MDM2 is measured by densitometric scanning or where covalent attachment of radio-labeled or otherwise tagged ubiquitin to MDM2 or p53 is measured; Western blot analysis, or other known techniques such as ELISA, immunoprecipitation, RIA, and the like. Candidate compounds that inhibit self-ubiquitylation of MDM2, as described in detail in the Examples which follow, are detected by a shift in molecular weight either of MDM2 or of ubiquitin that becomes covalently attached to MDM2. (See for example Lorrick K L., et al., Proc. Natl. Acad. Sci. USA, 1999, 96:11364-11369; Fang S., et al., J. Biol. Chem., 2000, 275(12)8945-8951; Ryan K M., et al., Curr. Op. Cell Biol., 2001, 13:332-337; which are herein incorporated by reference in their entirety). MDM2 self-ubiquitylation assays are run (see for example the results shown in FIGS. 2 and 3) in the presence or absence of a known amount of candidate compound. An aliquot of each of the test and control reactions are run on a standard SDS-PAGE gel. Test reactions whereby the candidate compounds inhibit the self-ubiquitylation of MDM2 will have a decrease in high molecular weight ubiquitylated MDM2.

In cellular assays, endogenous or transfected MDM2 is used. For transfected MDM2, ubiquitination is evaluated by an upward smear by anti-MDM2 Western blotting after resolution of cell lysates on SDS-PAGE. Alternatively, immunoprecipitation can be accomplished by subjecting lysates from cells (treated and untreated cells) to anti-MDM2, followed by Western Blotting and detecting ubiquitination by using anti-ubiquitin antibodies. Preferred screening methods comprise identifying a candidate compound based on assessment of p53 stabilization (e.g. half life of p53) and steady state levels, and the level of MDM2, as compared to a control, e.g. normal (non-cancer cells).

Steady-state levels of p53 and MDM2 in the cells can be determined by a number of approaches. For instance, lysates containing cellular protein can be immunoprecipitated with, for example, a rabbit anti-p53 polyclonal serum or MDM2 polyclonal serum, blotted onto polyvinylidenedifluoride (PVDF) membranes and probed with a monoclonal antibody cocktail comprising, for example, monoclonal antibodies to various epitopes of p53, or MDM2. Such antibodies are commercially available. Immunoblot analyses of cellular extracts, taken at different time points after treatment with a candidate compound is determinative of the half-life of p53 as compared to normal controls. Thus, increase or decrease in levels of p53 over periods of time is determinative of p53 stability based on its half-life and steady state levels. The lysates can be further purified, for example, by immunoprecipitation of p53 and/or MDM2 directly or indirectly of MDM2 and p53, or by affinity chromatography. Thus, candidate compounds that inhibit MDM2 ubiquitin ligase activity, can be screened for any effect on p53 stability.

Cell-based assays include model systems where primary human epithelial cells ("normal cells") are compared to the same cells expressing the adenovirus E1A oncogene ("transformed cells"). Activation of p53 was not toxic to normal cells, but activation of p53 in transformed cells induces p53-mediated apoptosis. High concentrations of wild type (wt) p53 protein can induce apoptosis in a variety of different tumor cells. Potential inhibitors of MDM2 would regulate the stability and function of p53 and MDM2. Preferably the assays measure number of cells undergoing apoptosis due to MDM2 induced p53 degradation in tumor cells in the presence or absence of candidate compounds as compared to normal cells in the presence or absence of candidate compounds. An increase in the number of these cells undergoing apoptosis in the presence of candidate compounds in tumor cells, as compared to normal untreated cells is indicative of a potential anti-tumor compound. Preferably a candidate compound increases apoptosis of tumor cells by at least 20% as compared to a control (no candidate compound administered), more preferably a candidate compound increases apoptosis of a tumor cell by at least about 30%. 40%, 50%, 60%, 70%, 80%, 90% or 100% as compared to a control (no candidate compound administered). That is, for example 80% increase of apoptosis refers to a decrease in the numbers of cells still surviving as compared to the controls.

Apoptosis can be measured by a variety of techniques. For example, apoptosis can be measured by determination of cell phenotype. Phenotype refers to how the cell looks, typically microscopically, but gross or macroscopic appearance can be observed. The phenotype changes depending on the growth rate of the cells. For instance, the microscopic morphology of cells that are rapidly dividing and growing is different than that of cells undergoing cell death by apoptosis. Determination of cell phenotype is well within the ability of one of ordinary skill in the art.

There are also a number of biochemical assays that can be used to detect apoptosis, such as "laddering" of the cellular DNA. When testing compounds for the ability to induce apoptosis, cell death (not cytostasis) is an endpoint of a compound application to the cell. A classic signature of apoptosis is the cleavage of nuclear DNA into nucleosomal subunits. On gels, this gives rise to the appearance of a ladder as nucleosomal units are sequentially cleaved from DNA. Observation of a classic DNA ladder is indicative of apoptosis. For example, cells are lysed and the high molecular weight DNA is removed by centrifugation. The aqueous phase is treated with proteinase K to digest proteins. After a phenol/chloroform extraction, the pellet is dissolved in deionized water and treated with 500 µg/ml RNaseA. The DNA is run on a 2% agarose minigel. Observation for a classic DNA ladder is made and a photograph can be taken. Cell death is verified by the demonstration of DNA as represented by the ladder configurations on the gel (see for example, White E., et al. 1984, J. Virol. 52:410). There are also a variety of other assays available for apoptosis such as "TUNEL" assays (see Gavrieli, Y., et al. (1992) J. Cell. Biol. 119:493).

As discussed above, the invention assays and screening methods for identification of other compounds possessing anti-cancer activity, including MDM2-specific and/or general inhibition of ubiquitin enzyme inhibitory activity. Thus, in accordance with the invention, methods are provided to screen candidate compounds which exhibit potential anti-cancer activity by measuring p53 stability in transformed cells and/or apoptosis and cell death.

All documents mentioned herein are incorporated herein in their entirety by reference.

The following non-limiting examples are illustrative of the invention.

EXAMPLE 1

High-Throughput Screening Assay

Method: GST-MDM2 is attached to glutathione-coated paramagnetic beads and the beads are washed. The beads are mixed with E1, E2 and ATP-containing buffer in 10 µl volume per one assay. Enzyme inhibitor is added in 5 µl. The reaction is started by adding 5 µl of ubiquitin and incubated for 1 hour at room temperature. EDTA and ORI-TAG™ labeled antibody against polyubiquitinated proteins in 130 µl is added and incubated for 1 hour at room temperature. The electrochemiluminesence (ECL)-generated signal is read in a M8 analyzer.

Result: The signal is dramatically reduced when mutant MDM2-H457S is used. XIAP, an unrelated RING-finger E3, demonstrated a 4-fold higher activity. MDM2 exhibited a signal to background ratio of ~100 in self-ubiquitylation assay. FIG. 1A is a graph showing that MDM2 exhibited a signal to background ratio of ~100 in self-ubiquitylation assay. Time course of MDM2 self-ubiquitylation revealed linear reaction kinetics and no benefit of shaking within the first 60 min. Samples were incubated at room temperature and not shaken for ease of automation as shown in FIG. 1B. FIG. 1C is a graph showing that the MDM2 assay signal is a function of time between addition of the antibody and measuring in M-8. The curve demonstrated the MDM2 assay signal as a function of time between addition of the antibody and measuring in M-8. The assay is stable overnight at room temperature.

EXAMPLE 2

In vitro Assays for Ubiquitination and Thiol-ester Bond Formation

Methods:

a. "Standard MDM2 in vitro Ubiguitination Assay" (E1+E2+E3 Assay)

1 pmole per experimental point of bacterially expressed GST-MDM2 (or GST-Nedd) was coupled to glutathione Sepharose (GS) for 30 minutes at room temperature with tumbling, followed by 3× wash with 50 mM Tris pH 7.5. Following this, 20 µl of 1× buffer was added (40 µl 10× reaction buffer*, 40 µl 10× PCK**, 320 µl dH$_2$O). The test compound in DMSO is then added to the desired concentration with an equal volume of DMSO used as a control. Samples are incubated with shaking for 1 hr at 23° C. To carry out the reaction, a pre-made cocktail of Rabbit E1 (Calbiochem #6620700)/UbcH5B/$^{32}$P Ub cocktail (1 µl/0.5 µl/1 µl) is added followed by 15 minutes shaking at 30° C. The reaction is terminated by addition of 8 µl 4× reducing SDS-PAGE loading buffer. After dissociating proteins from the beads at 100° C. for 2 minutes, samples are resolved on 6% PAGE followed by exposure of the dried gel to phosphor screen. Note: $^{32}$P Ub is derived from GST-Ub that has been engineered to include a PKA phosphorylation site. This fusion protein is purified on glutathione Sepharose, phosphorylated, following this, the $^{32}$P Ub ubiquitin is cleaved and purified away from the thrombin.

*10× Buffer
500 mM Tris (pH 7.5)
2 mM ATP
5 mM $MgCl_2$
1 mM DTT
10 mM creatine phosphate (Sigma P4635) (45 mg/10 ml).

**10× PCK
Sigma C7886, 1000 U, reconstitute in 200 µl 10 mM Tris pH 8.0.

b. "E1 only" Assay.

2 µl rabbit E1 +12 µl of 1× reaction buffer are mixed together with the test compound followed by addition of 1 µl of $^{32}$P Ub is added for 10 minutes at room temperature followed by resolution by SDS-PAGE under non-reducing conditions to maintain thiol-ester linkages and exposure as above.

c. E1+E2 Assay with Immobilized E2

20 pmoles of bacterially-expressed GST-UbcH5B is bound to GS for 30 minutes at room temperature after washing in 50 mM Tris pH 7.5. Twenty (20) µl of 1× reaction buffer is added. After incubation with the test compound for 1 hour at 23° C. the beads were washed with 50 mM Tris pH 7.5. This was followed by addition of Rabbit E1/32P Ub cocktail (1 µl/1 µl) followed by incubation at 1 hour shaking at 23° C. This is followed by resolution by SDS-PAGE under non-reducing conditions and exposure as above.

d. In Vitro R53 Ubiguitination Assay p53 protein from SaOS-p53 inducible cell lysate was purified from cells using GST-MDM2 (5 pmol) pre-bound to GS beads. Samples were then incubated with test compounds as above. Subsequently 2 µl rabbit E1, 1 µl UbcH5b, and 10 µg of ubiquitin were added. After reaction for 15 min at 23° C., samples were subject to SDS-PAGE under reducing conditions, transferred to nitrocellulose membranes and immunoblotted with anti-p53 (DO-1) followed by ECL using standard techniques.

Figure 2F:
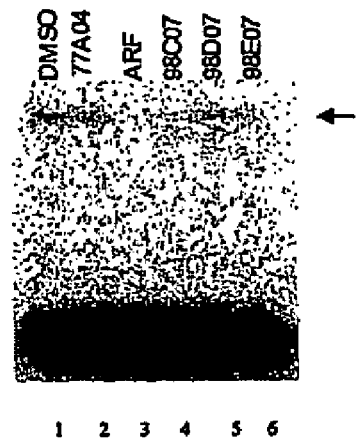
Figure 2G:
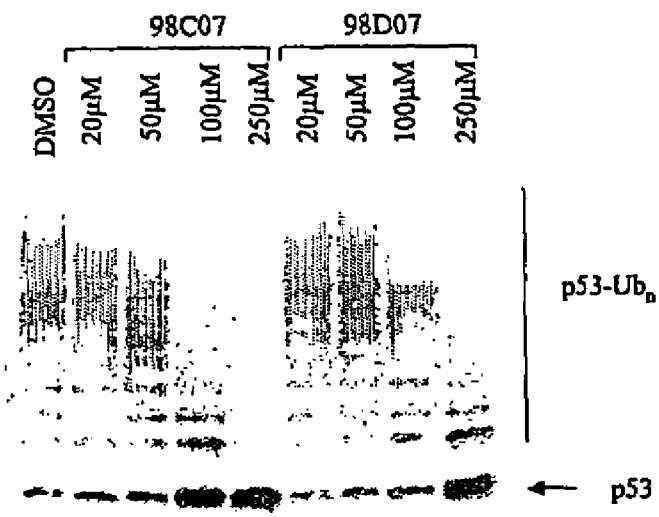

Results: Forty compounds from the initial high throughput screen were identified as exhibiting inhibition of MDM2 auto-ubiquitination activity of more than 50% and further tested in all in vitro assays identified above. Using the ARF peptide as a positive control for inhibition of MDM2 ubiquitination, these assays identified four compounds that showed an ability to significantly inhibit MDM2 E3 ligase (FIG. 2A lanes 7, 9, 10, 11). To determine whether the compounds were selective in their ability to inhibit MDM2, their effect on the activity of another unrelated E3 ligase, Nedd4 were tested. FIG. 2B shows typical results from that screen. Compound 98C07, 10-(-3-chloro-phenyl)-7-nitro-10H-pyrimido[4,5-b]quinoline-2,4-dione, shows some selectivity as an inhibitor of MDM2. By contrast, compound 97H10, 10-(4-chloro-phenyl)-7-nitro-10H-pyrimido[4,5-b]quinoline-2,4-dione inhibits all E3s and has been shown to block the activity of the E1 enzyme, rather than the E3 (see 2D below). FIG. 2C is an independent experiment further demonstrating the specificity of MDM2 by 98C07 (lane 2). In FIG. 2D and FIG. 2E the effect of compounds on the more proximal steps in the ubiquitination process, formation of thiol-ester linkages with E1 (FIG. 2D) and with E2 (FIG. 2E). As is evident, while at least one of the compounds inhibits more proximally, accounting for its lack of specificity, 98C07 inhibits neither thiol-ester linkages of ubiquitin with E1 nor E2. FIG. 2F shows inhibition of MDM2 auto-ubiquitination by two other close family members of 98C07. These are 98D07, 10-(-4-chloro-phenyl)-7-nitro-10H-pyrimido[4,5-b]quinoline-2,4-dione, and 98E07, 10-(-4-methyl-phenyl)-7-nitro-10H-pyrimido[4,5-b]quinoline-2,4-dione. Two of these compounds have been evaluated for inhibition of p53, 98C07 and 98D07 both exhibit significant dose-dependent inhibition of p53 ubiquitination after being pre-bound to GST-MDM2 (FIG. 2G).

EXAMPLE 3

In vivo Cell Based Assay for Accumulation of MDM2 and p53

Methods: Normal human fibroblast MRC-5 were chosen to determine whether the compounds from the high throughput screening can inhibit the E3 activity of Mdm2, i.e. stabilizing MDM2 and p53 in vivo. After being seeded in 12-well tissue culture cluster overnight, the cells were treated with 50 µM of the compounds for 8 hours. They were harvested with trypsin-EDTA, washed with PBS, and lysed with RIPA buffer. Following removal of insoluble pellet by centrifugation for 20 minutes at 10000 rpm, the lysate was separated on 4-20% gradient SDS-polyacrylamide gel and transferred onto nitrocellulose membrane. The membrane was then blotted with anti-p53 antibody (DO-1), anti-MDM2 antibodies (Ab-1 and Ab-2), anti-p27 (Santa Cruz), anti-Nedd4, and anti-p21Waf1 antibody. After extensive washing with PBS containing 0.5% Triton X-100, it was incubated with HRP-labeled donkey anti-mouse antibody and visualized using enhanced chemiluminescence.

Apoptosis and cell death were determined by FACS analysis of sub-G1 nuclei or counting trypan blue-positive cells under microscope. Caspase activity was measured using fluorogenic substrate Ac-DEVD-AFC and CytoFluor multi-well plate reader (PerSeptive Biosystems).

Figure 3A:
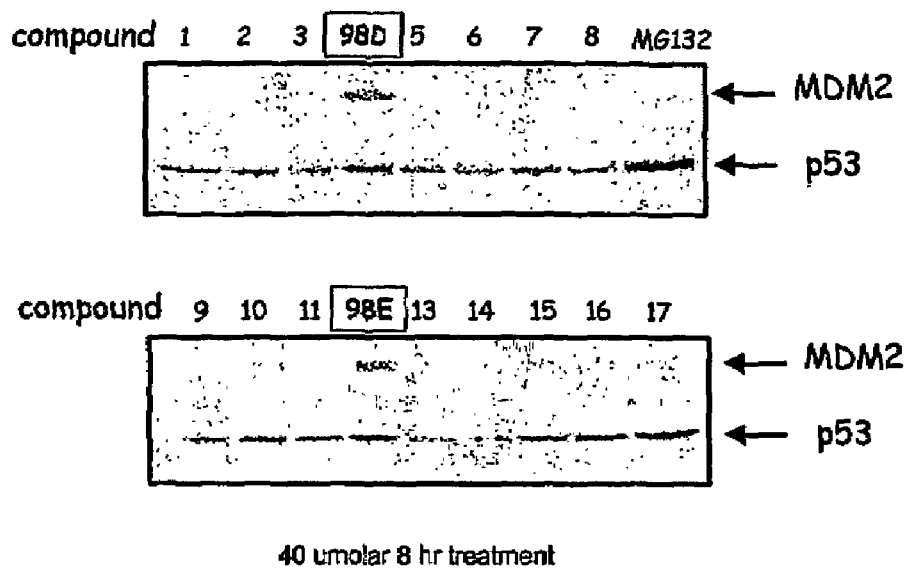
FIGS. 3A-3C show the results from the in vivo cell based assay for accumulation of MDM2 and p53. Normal human fibroblast MRC-5 were chosen to determine whether the compounds from the high throughput screening can inhibit the E3 activity of MDM2, i.e. stabilizing MDM2 and p53 in vivo. Compounds referred to as 98C07, 98D07, and 98E07 (10-(-4-methyl-phenyl)-7-nitro-10H-pyrimido[4,5-b]quinoline-2,4-dione) were all found to specifically increase MDM2 and p53 compared to a series of other compounds identified in the high throughput screen and were not further considered (FIG. 3A and FIG. 3B).
Figure 3B:
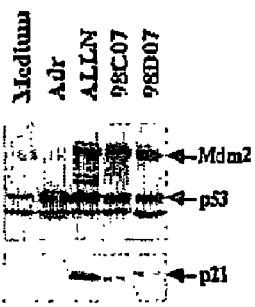
Figure 3C:
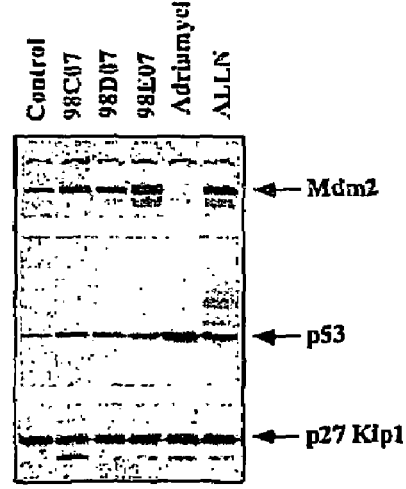

Results: Compounds referred to as 98C, 98D, and 98E were all found to specifically increase MDM2 and p53 compared to a series of other compounds identified in the high throughput screen and were not further considered (FIG. 3A and FIG. 3B). As shown in FIG. 3B, they all increased MDM2 and p53 levels in MRC-5 cells. The specificity of the compounds was also revealed by examining whether they affect the levels of the HECT domain E3 Nedd4 and p27, which is ubiquitinated by a RING finger-dependent SCF E3. As shown in FIG. 3B, the amounts of both Nedd4 and p27 were not changed significantly by any of the 98 family compounds. Moreover, while adriamycin increased only p53 and proteosome inhibitor (LLNL) accumulated MDM2, p53, and p21, these compounds only increased the amount of MDM2 and p53, but not p21, indicating they are specific for the E3 activity of MDM2 (FIG. 3C).

Figure 4:
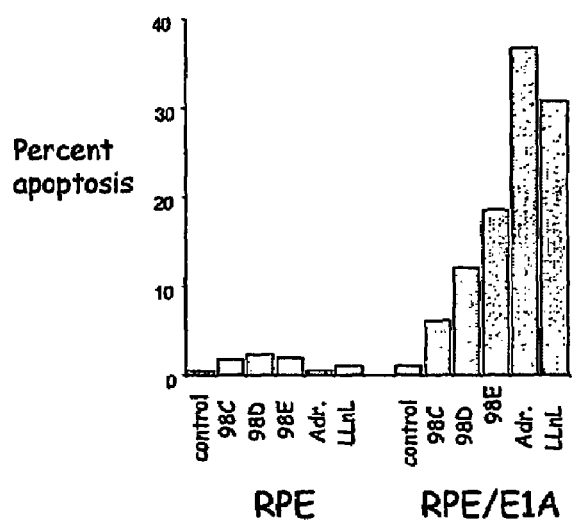
FIG. 4 shows a graph (left panel) and two gels (right panel) illustrating that the compounds stabilize p53 in untransformed cells (retinal pigment epithelial cells [RPE]) as well as transformed cells (RPE/E1A). However, only the transformed cells are sensitive to p53 and killed by the compounds.
Figure 4:
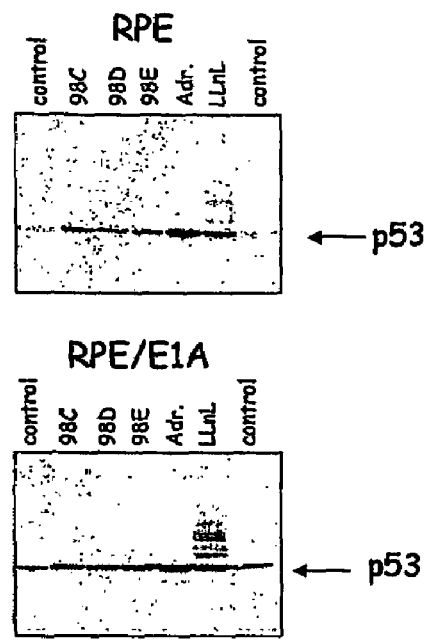
Figure 5A:
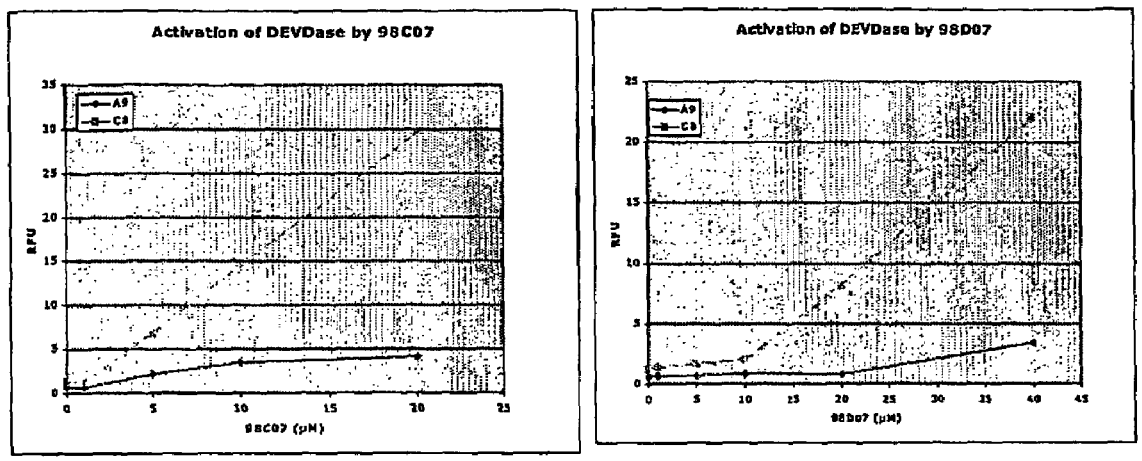
FIGS. 5A-5B are graphs showing results from an evaluation as to whether apoptosis stimulated by the compounds requires p53 expression. E1A and Ras transformed MEFs from cells either expressing p53 (C8) or p53$^{-/-}$ (A9) cells were compared in their capacity to activate effector caspases (FIG. 5a) and cell death (FIG. 5b).
Figure 5B:
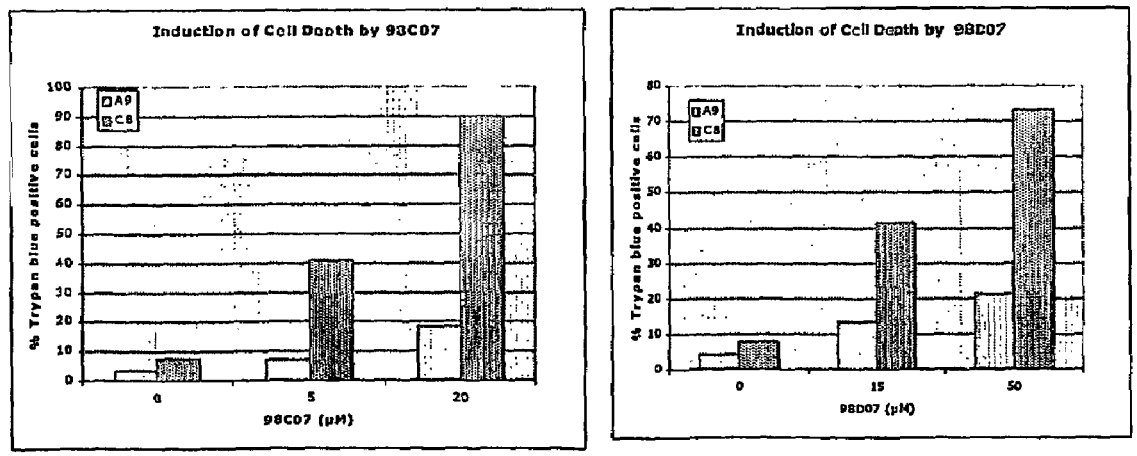

To assess whether the increased p53 can induce apoptosis in transformed cells, use was made of the retinal epithelial cells (RPE), which are resistant to p53-mediated apoptosis, and matched E1A-transformed RPE cells, which have become sensitive to p53-mediated apoptosis. As with adriamycin and the proteosome inhibitor, all three compounds markedly increased apoptosis in E1A transformed cells, while little affect on non-transformed RPE cells was observed (FIG. 4—left side). However, consistent with the predicted biological function of these compounds they all accumulated p53 in RPE cells regardless of whether they were transformed with E1A (FIG. 4—right side). To evaluate whether apoptosis stimulated by these compounds requires p53 expression, E1A and Ras transformed MEFs from cells either expressing p53 (C8) or p53$^{-/-}$ (A9) cells were compared in their capacity to activate effector caspases (FIG. 5a) and cell death (FIG. 5b).

Collectively, these results establish the capacity of these compounds to inhibit the ubiquitin ligase activity of MDM2 and the MDM2-mediated ubiquitination of p53. This is reflected in the stabilization of these molecules in cells and in relatively selective increased apoptosis in transformed cells over non-transformed cells and specifically in transformed cells that express p53.

EXAMPLE 4

Ubiquitin Ligase Method for GST-MDM-2 Fluorescent Detection

Glutathione sepharose beads (250 μl) are washed three times with 1 ml of wash buffer (50 mM Tris pH 8.0, 2mM DTT, 5mM $MgCl_2$, 100 mM NaCl, 1% Triton-X100) buffer and about 1.5 ml of bacterial lysate containing GST-MDM2 or variants thereof, and candidate compounds are added to the beads in separate vessels, e.g. a 1.5 ml eppendorf tube. The volumes used, are enough to conduct about 30 to about 100 reactions. The beads and each of the compounds are cultured at about 4° C. for about an hour and are continuously tumbled so as to keep the beads from settling and allow for maximum adsorbance of the compounds to the beads. The next steps include centrifugation, aspiration of the supernatant and washing in buffer (50 mM Tris pH 8.0, 2 mM DTT, 5 mM $MgCl_2$, 100 mM NaCl, 1% Triton-X100). This is followed by resuspension in 25 μl of reaction buffer (50 mM Tris pH 8.0, 2 mM DTT, 5 mM $MgCl_2$, 2 mM ATP) comprising 50 ng of E1, 1-2 μl of E2 and 1 μg of His-6-Ubiquitin. The mixtures are then incubated at 37° C. in a shaker at about 125 r.p.m. for up to about 30 minutes. The reactions are stopped by diluting in 0.8 mls of cold wash buffer comprising PBS 0.05% Tween 20. The supernatant is aspirated and India-horse radish peroxidase (500 μl of India-HRP 1:2000 diluted in wash buffer) is added and incubated for 15 minutes. After washing three times in wash buffer, 20 μl of each sample is assayed in 90 μl of Quantablue (Pierce). The mixture is excited at 320 nm and emissions are measured, and compared to controls, including a control lacking E2. Increased fluorescence relative to a control indicates ubiquitination.

The foregoing description of the invention is merely illustrative thereof, and it is understood that variations and modifications can be effected without departing from the spirit or scope of the invention as set forth in the following claims.

What is claimed is:

1. A method of treating cancer comprising administering to a subject suffering from cancer a compound of the following Formula IV

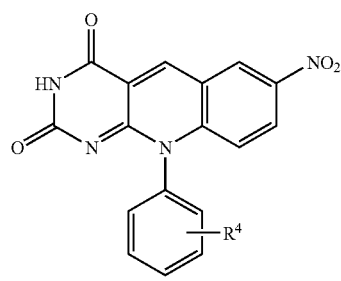

IV wherein $R^4$ is selected from the group consisting of amino, halogen, hydroxy, $C_{2-6}$alkenyl, $C_{2-6}$alkynyl, $C_{1-6}$alkoxy, or mono or di($C_{1-6}$alkyl)amino; and pharmaceutically acceptable salts thereof and wherein the cells of said cancer retain a wild type p53 gene.

2. The method of claim 1 wherein $R^4$ is amino.

3. The method of claim 1 wherein $R^4$ is halogen.

4. The method of claim 1 wherein $R^4$ is hydroxyl.

5. The method of claim 1 wherein $R^4$ is $C_{2-6}$alkenyl or $C_{2-6}$alkynyl.

6. The method of claim 1 wherein $R^4$ is $C_{1-6}$alkoxy.

7. The method of claim 1 wherein $R^4$ is mono or di($C_{1-6}$alkyl)amino.

8. The method of claim 1 wherein $R^4$ is selected from the group consisting of a chloro or fluoro group, and $R^4$ is attached to the 3 or 4 position of the phenyl ring.

9. The method of claim 1 wherein $R^4$ is chloro and is attached to the 3 or 4 position of the phenyl ring.

10. The method of claim 1 wherein $R^4$ is fluoro and is attached to the 3 or 4 position of the phenyl ring.

11. The method of claim 1 wherein $R^4$ is methyl and is attached to the 3 or 4 position of the phenyl ring.

12. The method of claim 1 wherein the compound is selected from the group consisting of 10-(3-chloro-phenyl)-7-nitro-10H-pyrimido[4,5-b]quinoline-2,4-dione, and 10-(4-chloro-phenyl)-7-nitro-10H-pyrimido[4,5-b]quinoline-2,4-dione; and pharmaceutically acceptable salts thereof.

13. The method of claim 1 wherein the subject has a solid tumor.

14. The method of claim 1 wherein the subject has a disseminated cancer.

15. The method of claim 1 wherein the patient is a mammal.

16. The method of claim 1 wherein the patient is a primate or human.

17. A method of treating cancer comprising:
administering a compound of the following Formula IV to a subject suffering from cancer of the colon, prostate, breast or skin:

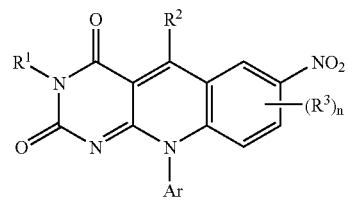

I wherein $R^4$ is selected from the group consisting of amino, halogen, hydroxy, $C_{2-6}$alkenyl, $C_{2-6}$alkynyl, $C_{1-6}$alkoxy, or mono or di($C_{1-6}$alkyl)amino; and pharmaceutically acceptable salts thereof and wherein the cells of said cancer retain a wild type p53 gene.

18. The method of claim 17 wherein $R^4$ is amino.

19. The method of claim 17 wherein $R^4$ is halogen.

20. The method of claim 17 wherein $R^4$ is hydroxyl.

21. The method of claim 17 wherein the compound is selected from the group consisting of 10-(3-chloro-phenyl)-7-nitro-10H-pyrimido[4,5-b]quinoline-2,4-dione, and 10-(4-chloro-phenyl)-7-nitro-10H-pyrimido[4,5-b]quinoline-2,4-dione; and pharmaceutically acceptable salts thereof.

22. The method of claim 17 wherein the subject is suffering from breast cancer.

* * * * *